US007659317B2

(12) United States Patent
Eriksson et al.

(10) Patent No.: US 7,659,317 B2
(45) Date of Patent: Feb. 9, 2010

(54) METHODS TO PREPARE CARBON-ISOTOPE LABELED ORGANOHALIDES WITH HIGH SPECIFIC RADIOACTIVITY FROM CARBON-ISOTOPE MONOXIDE

(75) Inventors: Jonas Eriksson, Uppsala (SE); Bengt Langstrom, Uppsala (SE); Gunnar Antoni, Uppsala (SE)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 10/592,555

(22) PCT Filed: Mar. 10, 2005

(86) PCT No.: PCT/IB2005/000601

§ 371 (c)(1),
(2), (4) Date: Sep. 12, 2006

(87) PCT Pub. No.: WO2005/090267

PCT Pub. Date: Sep. 29, 2005

(65) Prior Publication Data

US 2007/0203251 A1    Aug. 30, 2007

Related U.S. Application Data

(60) Provisional application No. 60/553,802, filed on Mar. 17, 2004, provisional application No. 60/579,930, filed on Jun. 15, 2004.

(51) Int. Cl.
*C07C 319/02* (2006.01)
*C07C 17/00* (2006.01)
*C07C 27/06* (2006.01)

(52) U.S. Cl. .................. 518/700; 562/602; 564/510; 568/56

(58) Field of Classification Search ................. 518/700; 562/602; 564/510; 568/56; 570/240
See application file for complete search history.

(56) References Cited

FOREIGN PATENT DOCUMENTS

WO      02/102711      12/2002
WO      WO 2102711 A1 *   12/2002

OTHER PUBLICATIONS

T. Kihlberg, "11C Carbon Monoxide in the Synthesis of Carbonyl Compounds Using Palladium or Selenium Mediated Reactions" J. Label. Compd. Radiopharm, vol. 42, No. S1, 1999 pp. S86-S88.
Chemical Abstracts Service, Columbus Ohio US, Amarnath, Venkataraman et.al, "Reactions of 4-Hydroxy-2(E)-nonenal and Related Aldehydes with Proteins Studied by Carbon-13 Nuclear Magnetic Resonance Spectroscopy" XP002346621: Database accession No. 1998:240164.
Chemical Abstracts Service, Columbus Ohio US Pardoen, J.A., et.al. "Synthesis of 8-,9-,12-, and 13-mono-13C-retinal" XP002346622 Database accession No. 1986:6050.
Chemical Abstracts Service, Columbus Ohio US Peng, Sheng, et.al. "Synthesis of Site-Specifically Labeled Arachidonic Acids as Mechanistic Probes for Prostaglandin H Synthase" XP002346623 Database accession No. 2004:42412.
Chemical Abstracts Service, Columbus Ohio US Maggs, James L. et.al. "Synthesis of DL-2-14C Octan-2-Sulfate and Sulfur-35-labeled L(+)-and L(−)-octan-2-sulfate" XP002346624 Database accession No. 1981:191602.
Chemical Abstracts Service, Columbus Ohio US Tang, D.Y. et.al. "Carbon-11 labeled octanal and benzaldehyde" XP002346625 Database accession No. 1980:22190.
Chemical Abstracts Service, Columbus Ohio US Schmit, J.P., et.al., "Synthesis of 2,4-dihydroxy-6-pentylbenzoic-6-14C acid ethyl ester (olivetolic-6-14C acid ethyl ester)" XP002346626 Database accession No. 1976:58850.
Chemical Abstracts Service, Columbus Ohio US Ewing, D.F. "Abnormal trend in J(13C-CH) values in some aldehydes" XP002346627 Database accession No. 1971:475617.
J. Erkisson "Synthesis of 1-11C-Ethyl Iodide from 11C-carbon monoxide and its application in alkylation reactions" J. Label Compd. Radiopharm, vo. 47, 2004 pp. 723-731.
Beilstein Institute For Organic Chemistry, Frankfurt-Main, DE: 1997 XP002346628 database accession No. 4715075 abstract & Langstrom B. : Acta Chem. Scan., vol. 51, No. 3, 1997 pp. 418-425.
Beilstein Institute For Organic Chemistry, Frankfurt-Main, DE 1989 XP002346629 database accession No. 1789034 abstract & Nakamura H. Chem. Pharm. Bull, vol. 37, No. 12, pp. 3376-3379.
Beilstein Institute For Organic Chemistry, Frankfurt-Main, DE 1993, XP002346630 database accession No. 1848877 abstract & Ohmomo Y.: Chem. Pharm. Bull., vol. 41, No. 11, 1993, pp. 1994-1997.
Beilstein Institute For Organic Chemistry, Frankfurt-Main, DE 2001, XP002346631 database accession No. 8823527 abstract & Ackermann U. J. Label. Compd. Pharm., vol. 45, No. 2, 2002, pp. 157-166.
Beilstein Institute For Organic Chemistry, Frankfurt-Main, DE XP002346632 Database accession No. 5191602 abstract & Sandell Y: J. Label. Compd. Radiopharm., vol. 43, No. 10, 2000 pp. 1033-1046.
Beilstein Institute For Organic Chemistry, Frankfurt-Main, DE 1997, XP002346633 database accession No. 4819358 abstract & Mathis C.A. J. Label. Compd. Radiohpharm., vol. 40, 1997, pp. 563-564.
Beilstein Institute For Organic Chemistry, Frankfurt-Main, DE 1997 XP002346634 database accession No. 4819360 abstract & Mathis C.A. J. Label. Compd. Radiopharm. vol. 40, 1997 pp. 563-564.

(Continued)

*Primary Examiner*—Shailendra Kumar
(74) *Attorney, Agent, or Firm*—Craig Bohlken

(57) ABSTRACT

Methods and reagents for labeling synthesis of organohalides by transition metal mediated carbonylation reactions using carbon-isotope labeled carbon monoxide are provided. The resultant carbon-isotope labeled organohalides are useful as radiopharmaceuticals, especially for use as precursors in Positron Emission Tomography (PET). Associated PET tracers and kits for PET studies are also provided.

13 Claims, 3 Drawing Sheets

OTHER PUBLICATIONS

Beilstein Institute For Organic Chemistry, Frankfurt-Main, DE XP002346635 database accession No. 5214974 abstract & Holschbach M. J. Label. Compd. Radiopharm., vol. 42, No. 1, 1999, pp. S89-S91.

Beilstein Institute For Organic Chemistry, Frankfurt-Main, DE 2000, XP002346636 database accession No. 5220019 abstract & Hoschbach M. J. Label. Compd. Radiopharm., vol. 42, No. 1, 1999 pp. S89-S91.

Beilstein Institute For Organic Chemistry, Frankfurt-Main, DE 2000, XP002346637 database accession No. 8308152 abstract & Khanum N., J. Label. Compd. Radiopharm. vol. 42, No. 1, 1999, pp. S451-S453.

Beilstein Institute For Organic Chemistry, Frankfurt-Main, DE 1995, XP002346638 database accession No. 7017500 abstract & Kihlbert T., Acta.Chem. Scand, vol. 48, No. 7, 1994 pp. 570-577.

Beilstein Institute For Organic Chemistry, Frankfurt-Main, DE 2001, XP002346639 database accession No. 8677582 abstract & Wuest F. J. Label. Compd. Radiopharm., vol. 43, No. 13, 2000, pp. 1289-1300.

Langstrom, B. "Palladium-mediated Carboxylation of Aryl Halides (triflates) or Benzyl Halides using 13C/11C Carbon monoxide with tetrabutylammonium hydroxide or trimethylphenyl ammonium hydroxide" J. Chem. Soc., Perkin Trans 1, 2002, pp. 2256-2259.

Chemical Abstracts Service, Columbus, Ohio, US, Pippel, Daniel J., et.al., "Kinetics and mechanism of the (−)-Sparteine-mediated deprotonation of (E)-N-Boc-N-(p-methoxyphenyl)-3-cyclohexyl allylamine" XP002346708 retreived from STN database accession No. 2001:315901 abstract & Journal of the American chemical society, 123(21) 4919-4927.

Chemical Abstracts Service, Columbus Ohio, US, Schwab, John M. et.al. "beta-hydroxydecanoyl thioester dehydrase. Complete characterization of the fate of the "suicide" substrate 3-decynoyl-NAC" XP002346709 retrieved from STN database accession No. 1986: 474868 abstract & Journal of the American chemical society, 108(17), 5309-16.

Chemical Abstracts Service, Columbus, Ohion, US, Sahlberg, Christer, et.al. "Allenes and acetylenes. Part XXVII. Synthesis of radioactively labeled allenic MAO-inhibitors" XP002346710 retrieved from STN database accession No. 1984:5957 abstract & acta Pharmaceutica Suecica, 20(3), 233-8.

Chemical Abstracts Service, Columbus, Ohio, US, Franke, Wilfried, et.al. "Degenerate carbon transposition isomerization of the cyclopentyl cation in the gas phase. Experimental and theoretical evidence for the existence of a pyramidal C5H9+ cation in the unimolecular ethylene elimination" XP002346711 retrieved from STN database accession No. 1981:567957 abstract & Chemische Berichte, 114(8), 2808-24.

PCT/IB2005/000601 Int'l Search Report & Written Opinion dated Oct. 10, 2005.

* cited by examiner

US 7,659,317 B2

METHODS TO PREPARE CARBON-ISOTOPE LABELED ORGANOHALIDES WITH HIGH SPECIFIC RADIOACTIVITY FROM CARBON-ISOTOPE MONOXIDE

This application is a 371 of PCT/IB05/00601, filed Mar. 10, 2005 which claims benefit of 60/553,802, filed Mar. 17, 2004 and claims benefit of 60/579,930, filed Jun. 15, 2004.

FIELD OF THE INVENTION

The present invention relates to diagnostic and radiodiagnostic agents, including biologically active compounds labeled with positron-emitting nuclides. It further relates to a method for the use of carbon-isotope monoxide in labeling synthesis. More specifically, the invention relates to a method for producing an [$^{11}$C]carbon monoxide enriched gas mixture from an initial [$^{11}$C]carbon dioxide gas mixture, and using the produced gas mixture in labeling synthesis of organohalides by transition metal mediated carbonylation reactions. Radiolabeled organohalides according to the present invention are useful as radiopharmaceuticals, specifically for use precursors in the production of tracers in Positron Emission Tomography (PET).

BACKGROUND OF THE INVENTION

Tracers labeled with short-lived positron emitting radionuclides (e.g. $^{11}$C, $t_{1/2}$=20.3 min) are frequently used in various non-invasive in vivo studies in combination with positron emission tomography (PET). Because of the radioactivity, the short half-lives and the submicromolar amounts of the labeled substances, extraordinary synthetic procedures are required for the production of these tracers. An important part of the elaboration of these procedures is development and handling of new $^{11}$C-labelled precursors. This is important not only for labeling new types of compounds, but also for increasing the possibility of labeling a given compound in different positions.

During the last two decades carbonylation chemistry using carbon monoxide has developed significantly. The recent development of methods such as palladium-catalyzed carbonylative coupling reactions has provided a mild and efficient tool for the transformation of carbon monoxide into different carbonyl compounds.

Carbonylation reactions using [$^{11}$C]carbon monoxide has a primary value for PET-tracer synthesis since biologically active substances often contain carbonyl groups or functionalities that can be derived from a carbonyl group. The syntheses are tolerant to most functional groups, which means that complex building blocks can be assembled in the carbonylation step to yield the target compound. This is particularly valuable in PET-tracer synthesis where the unlabelled substrates should be combined with the labeled precursor as late as possible in the reaction sequence, in order to decrease synthesis-time and thus optimize the uncorrected radiochemical yield.

When compounds are labeled with $^{11}$C, it is usually important to maximize specific radioactivity. In order to achieve this, the isotopic dilution and the synthesis time must be minimized. Isotopic dilution from atmospheric carbon dioxide may be substantial when [$^{11}$C]carbon dioxide is used in a labeling reaction. Due to the low reactivity and atmospheric concentration of carbon monoxide (0.1 ppm vs. $3.4 \times 10^4$ ppm for $CO_2$), this problem is reduced with reactions using [$^{11}$C] carbon monoxide.

The synthesis of [$^{11}$C]carbon monoxide from [$^{11}$C]carbon dioxide using a heated column containing reducing agents such as zinc, charcoal or molybdenum has been described previously in several publications. Although [$^{11}$C]carbon monoxide was one of the first $^{11}$C-labelled compounds to be applied in tracer experiments in human, it has until recently not found any practical use in the production of PET-tracers. One reason for this is the low solubility and relative slow reaction rate of [$^{11}$C]carbon monoxide which causes low trapping efficiency in reaction media. The general procedure using precursors such as [$^{11}$C]methyl iodide, [$^{11}$C]hydrogen cyanide or [$^{11}$C]carbon dioxide is to transfer the radioactivity in a gas-phase, and trap the radioactivity by leading the gas stream through a reaction medium. Until recently this has been the only accessible procedure to handle [$^{11}$C]carbon monoxide in labeling synthesis. With this approach, the main part of the labeling syntheses with [$^{11}$C]carbon monoxide can be expected to give a very low yield or fail completely.

There are only a few examples of practically valuable $^{11}$C-labelling syntheses using high pressure techniques (>300 bar). In principal, high pressures can be utilized for increasing reaction rates and minimizing the amounts of reagents. One problem with this approach is how to confine the labeled precursor in a small high-pressure reactor. Another problem is the construction of the reactor. If a common column type of reactor is used (i.e. a cylinder with tubing attached to each end), the gas-phase will actually become efficiently excluded from the liquid phase at pressurization. The reason is that the gas-phase, in contracted form, will escape into the attached tubing and away from the bulk amount of the liquid reagent.

The cold-trap technique is widely used in the handling of $^{11}$C-labelled precursors, particularly in the case of [$^{11}$C]carbon dioxide. The procedure has, however, only been performed in one single step and the labeled compound was always released in a continuous gas-stream simultaneous with the heating of the cold-trap. Furthermore, the volume of the material used to trap the labeled compound has been relative large in relation to the system to which the labeled compound has been transferred. Thus, the option of using this technique for radical concentration of the labeled compound and miniaturization of synthesis systems has not been explored. This is especially noteworthy in view of the fact that the amount of a $^{11}$C-labelled compound usually is in the range 20-60 nmol.

Recent technical development for the production and use of [$^{11}$C]carbon monoxide has made this compound useful in labeling synthesis. WO 02/102711 describes a system and a method for the production and use of a carbon-isotope monoxide enriched gas-mixture from an initial carbon-isotope dioxide gas mixture. [$^{11}$C]carbon monoxide may be obtained in high radiochemical yield from cyclotron produced [$^{11}$C] carbon dioxide and can be used to yield target compounds with high specific radioactivity. This reactor overcomes the difficulties listed above and is useful in synthesis of $^{11}$C-labelled compounds using [$^{11}$C]carbon monoxide in palladium or selenium mediated reaction. With such method, a broad array of carbonyl compounds can be labeled (Kihlberg, T.; Langstrom, B. J., Org. Chem. 64, 1999, 9201-9205; Kihlberg, T., Karimi, F., Langstrom, B., J. Org. Chem. 67, 2002, 3687-3692).

Such labeled carbonyl compounds have opened an avenue to synthesize a number of pharmaceutically important tracers for applications in PET. New carbon-isotope labeling methods are needed to render possible for new compounds to be used with PET applications. It is notable that carbon-isotope labeled organohalides can be utilized in alkylation reactions and are therefore valuable precursor in the production of PET tracers. Each type of labeled organohalide can generally be used to label a large number of different compounds. With easy access to good quality carbon-isotope labeled alkylating agents such as alkyl halides, or aromatic halides, it is possible to label a particular compound that structurally possess any such group in a position suitable for labeling. Furthermore, it also becomes possible to change physical and biological properties of the labeled compounds by modifying its structure through the use of different labeled organohalides as alkylating agents. Thus, an increased availability of such precursors is an efficient way of increasing the number of compounds that can be labeled.

Therefore, there is a need for new methods of synthesizing more versatile labeled organohalides as reaction precursors or PET tracers by using [$^{11}$C]carbon monoxide with high specific radioactivity, as it is important in PET applications. It would further increase the utility of [$^{11}$C]carbon monoxide in preparing useful PET tracers.

Discussion or citation of a reference herein shall not be construed as an admission that such reference is prior art to the present invention.

SUMMARY OF THE INVENTION

The present invention provides a method for labeling synthesis of an organohalide compound, comprising:

(a) providing a high pressure reaction chamber having a liquid/gas inlet and a gas inlet in a bottom surface thereof, (b) providing a substrate solution to be labeled mixed with a transition metal complex, (c) providing $H_2$ gas or HOR, with optional water, where R is independently linear or lower cyclic alkyl or aryl, (d) introducing a carbon-isotope monoxide enriched gas-mixture into the reaction chamber via the gas inlet, (e) introducing at high-pressure said $H_2$ gas or HOR, with optional water, into the reaction chamber via the liquid/gas inlet, (f) introducing at high-pressure said substrate solution mixed with transition metal complex into the reaction chamber via the liquid/gas inlet, (g) waiting a predetermined time while the labeling synthesis occur, and (h) removing the labeled compounds from the reaction chamber, (i) reducing the labeled compounds to alcohol, (j) substituting with a halogen atom to obtain the labeled organohalides.

The present invention further provides labeled organolhalide compounds produced by the method of the instant invention.

In yet another embodiment, the invention also provides [$^{11}$C]-labeled compounds using labeled organohalide as a precursor. In still another embodiment, the invention provides kits for use as PET tracers comprising such [$^{11}$]-labeled compounds.

DETAILED DESCRIPTION OF THE INVENTION

One object of the invention is to provide a method and a system for production of and use of carbon-isotope monoxide in labeling synthesis that overcomes the drawbacks of the prior art devices. This is achieved by the method and system claimed in the invention.

One advantage with such a method and system is that nearly quantitative conversion of carbon-isotope monoxide into labeled products can be accomplished.

There are several other advantages with the present method and system. The high-pressure technique makes it possible to use low boiling solvents such as diethyl ether at high temperatures (e.g. 200° C.). The use of a closed system consisting of materials that prevents gas diffuision, increases the stability of sensitive compounds and could be advantageous also with respect to Good Manufacturing Practice (GMP).

Still other advantages are achieved in that the resulting labeled compound is highly concentrated, and that the miniaturization of the synthesis system facilitates automation, rapid synthesis and purification, and optimization of specific radioactivity through minimization of isotopic dilution.

Most important is the opening of completely new synthesis possibilities, as exemplified by the present invention.

Embodiments of the invention will now be described with reference to the figures.

The term carbon-isotope that is used throughout this application preferably refers to $^{11}$C, but it should be understood that $^{11}$C may be substituted by other carbon-isotopes, such as $^{13}$C and $^{14}$C, if desired.

Figure 1:
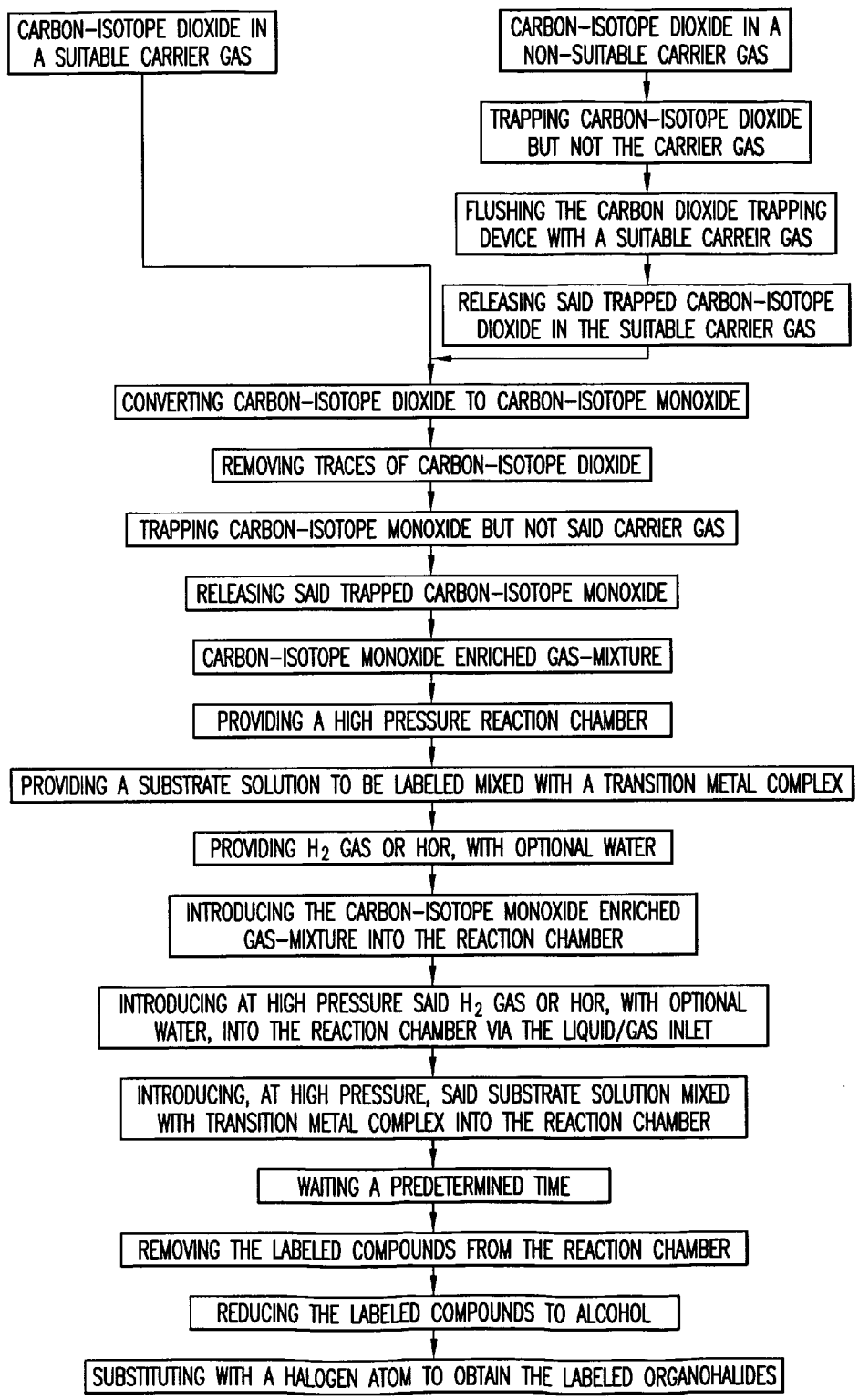
FIG. 1 shows a flow chart over the method according to the invention.

FIG. 1 shows a flow chart over the method according to the invention, which firstly comprises production of a carbon-isotope monoxide enriched gas-mixture and secondly a labeling synthesis procedure. More in detail the production part of the method comprises the steps of:

Providing carbon-isotope dioxide in a suitable carrier gas of a type that will be described in detail below.

Converting carbon-isotope dioxide to carbon-isotope monoxide by introducing said gas mixture in a reactor device which will be described in detail below.

Removing traces of carbon-isotope dioxide by flooding the converted gas-mixture through a carbon dioxide removal device wherein carbon-isotope dioxide is trapped but not carbon-isotope monoxide nor the carrier gas, The carbon dioxide removal device will be described in detail below.

Trapping carbon-isotope monoxide in a carbon monoxide trapping device, wherein carbon-isotope monoxide is trapped but not said carrier gas. The carbon monoxide trapping device will be described in detail below.

Releasing said trapped carbon-isotope monoxide from said trapping device, whereby a volume of carbon-isotope monoxide enriched gas-mixture is achieved.

The production step may further comprise a step of changing carrier gas for the initial carbon-isotope dioxide gas mixture if the initial carbon-isotope dioxide gas mixture is comprised of carbon-isotope dioxide and a first carrier gas not suitable as carrier gas for carbon monoxide due to similar molecular properties or the like, such as nitrogen. More in detail the step of providing carbon-isotope dioxide in a suitable second carrier gas such as He, Ar, comprises the steps of:

Flooding the initial carbon-isotope dioxide gas mixture through a carbon dioxide trapping device, wherein carbon-isotope dioxide is trapped but not said first carrier gas. The carbon dioxide trapping device will be described in detail below.

Flushing said carbon dioxide trapping device with said suitable second carrier gas to remove the remainders of said first carrier gas.

Releasing said trapped carbon-isotope dioxide in said suitable second carrier gas.

The labeling synthesis step that may follow the production step utilizes the produced carbon-isotope monoxide enriched gas-mixture as labeling reactant. More in detail the step of labeling synthesis comprises the steps of:

Providing a high pressure reaction chamber having a liquid/gas reagent inlet and a gas inlet in a bottom surface thereof. The reaction chamber will be described in detail below.

Providing a substrate solution to be labeled mixed with a transition metal complex.

Providing $H_2$ gas, with optional water or HOR, where R is independently linear or lower cyclic alkyl or aryl.

Introducing the carbon-isotope monoxide enriched gas-mixture into the reaction chamber via the gas inlet.

Introducing, at high pressure, said $H_2$ gas, with optional water or HOR, into the reaction chamber via the liquid/gas inlet.

Introducing, at high pressure, said substrate solution mixed with transition metal complex into the reaction chamber via the liquid reagent inlet.

Waiting a predetermined time while the labeling synthesis occurs.

Removing the solution of labeled compound from the reaction chamber.

Reducing the labeled compounds to alcohol.

Substituting with a halogen atom to obtain organohalide compounds.

The step of waiting a predetermined time may further comprise adjusting the temperature of the reaction chamber such that the labeling synthesis is enhanced.

Figure 2:
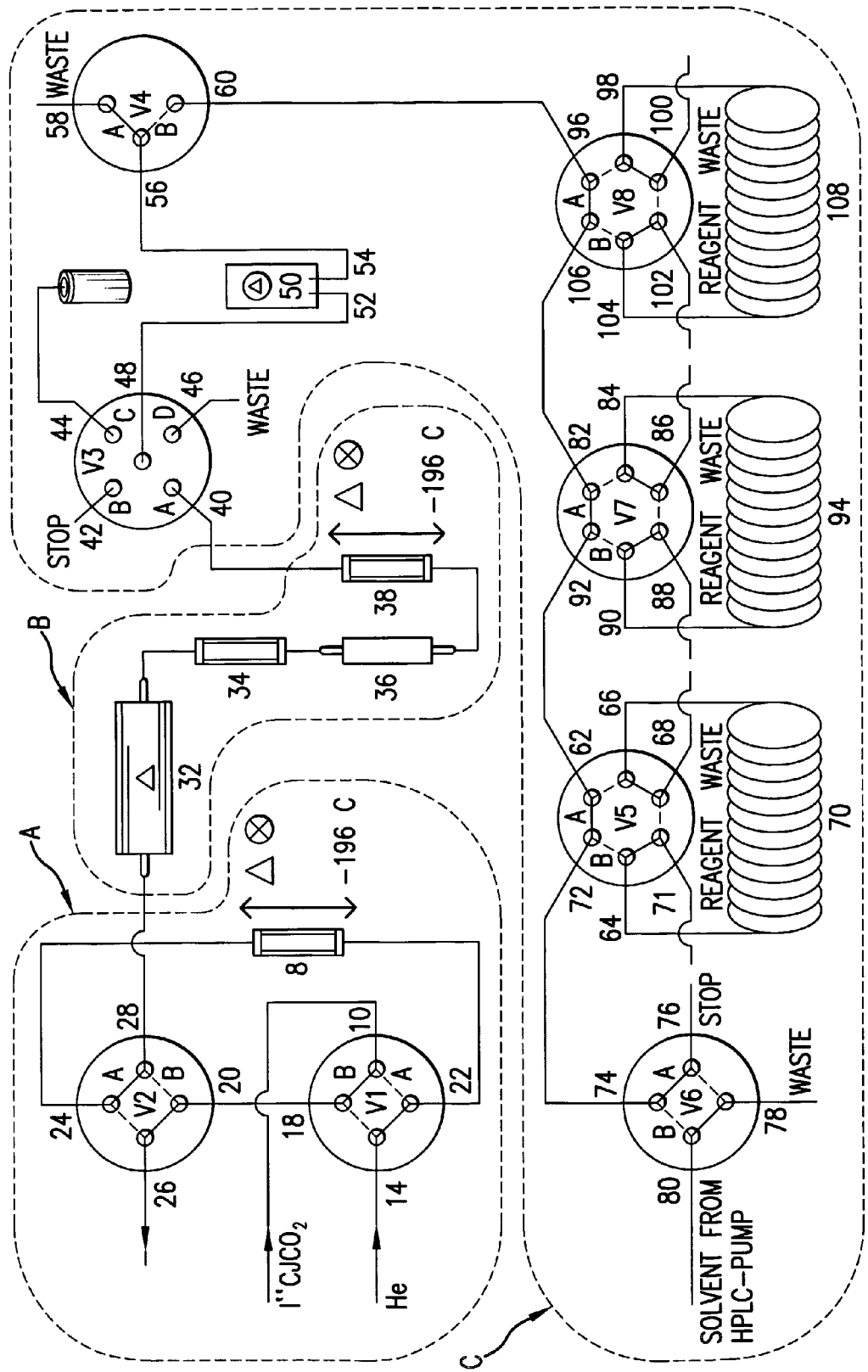
FIG. 2 is a schematic view of a carbon-isotope monoxide production and labeling-system according to the invention.

FIG. 2 schematically shows a [$^{11}$C]carbon dioxide production and labeling-system according to the present invention. The system is comprised of three main blocks, each handling one of the three main steps of the method of production and labeling:

Block A is used to perform a change of carrier gas for an initial carbon-isotope dioxide gas mixture, if the initial carbon-isotope dioxide gas mixture is comprised of carbon-isotope dioxide and a first carrier gas not suitable as carrier gas for carbon monoxide.

Block B is used to perform the conversion from carbon-isotope dioxide to carbon-isotope monoxide, and purify and concentrate the converted carbon-isotope monoxide gas mixture.

Block C is used to perform the carbon-isotope monoxide labeling synthesis.

Block A is normally needed due to the fact that carbon-isotope dioxide usually is produced using the $14N(p,\alpha)^{11}C$ reaction in a target gas containing nitrogen and 0.1% oxygen, bombarded with 17 MeV protons, whereby the initial carbon-isotope dioxide gas mixture comprises nitrogen as carrier gas. However, compared with carbon monoxide, nitrogen show certain similarities in molecular properties that makes it difficult to separate them from each other, e.g. in a trapping device or the like, whereby it is difficult to increase the concentration of carbon-isotope monoxide in such a gas mixture. Suitable carrier gases may instead be helium, argon or the like. Block A can also used to change the pressure of the carrier gas (e.g. from 1 to 4 bar), in case the external system does not tolerate the gas pressure needed in block B and C. In an alternative embodiment the initial carbon-isotope dioxide gas mixture is comprised of carbon-isotope dioxide and a first carrier gas that is well suited as carrier gas for carbon monoxide, whereby the block A may be simplified or even excluded.

According to a preferred embodiment (FIG. 2), block A is comprised of a first valve V1, a carbon dioxide trapping device 8, and a second valve V2.

The first valve V1 has a carbon dioxide inlet 10 connected to a source of initial carbon-isotope dioxide gas mixture 12, a carrier gas inlet 14 connected to a source of suitable carrier gas 16, such as helium, argon and the like. The first valve V1 further has a first outlet 18 connected to a first inlet 20 of the second valve V2, and a second outlet 22 connected to the carbon dioxide trapping device 8. The valve V1 may be operated in two modes A, B, in mode A the carbon dioxide inlet 10 is connected to the first outlet 18 and the carrier gas inlet 14 is connected to the second outlet 22, and in mode B the carbon dioxide inlet 10 is connected to the second outlet 22 and the carrier gas inlet 14 is connected to the first outlet 18.

In addition to the first inlet 20, the second valve V2 has a second inlet 24 connected to the carbon dioxide trapping device 8. The second valve V2 further has a waste outlet 26, and a product outlet 28 connected to a product inlet 30 of block B. The valve V2 may be operated in two modes A, B, in mode A the first inlet 20 is connected to the waste outlet 26 and the second inlet 24 is connected to the product outlet 28, and in mode B the first inlet 20 is connected to the product outlet 28 and the second inlet 24 is connected to the waste outlet 26.

The carbon dioxide trapping device 8 is a device wherein carbon dioxide is trapped but not said first carrier gas, which trapped carbon dioxide thereafter may be released in a controlled manner. This may preferably be achieved by using a cold trap, such as a column containing a material which in a cold state, (e.g. $-196°$ C. as in liquid nitrogen or $-186°$ C. as in liquid argon) selectively trap carbon dioxide and in a warm state (e.g. $+50°$ C.) releases the trapped carbon dioxide. (In this text the expression "cold trap" is not restricted to the use of cryogenics. Thus, materials that trap the topical compound at room temperature and release it at a higher temperature are included). Examples of suitable material are silica and porapac Q®. The trapping behavior of a silica-column or a porapac-column is related to dipole-dipole interactions or possibly Van der Waal interactions. The said column 8 is preferably formed such that the volume of the trapping material is to be large enough to efficiently trap (>95%) the carbon-isotope dioxide, and small enough not to prolong the transfer of trapped carbon dioxide to block B. In the case of porapac Q® and a flow of 100 ml nitrogen/min, the volume should be 50-150 µl. The cooling and heating of the carbon dioxide trapping device 8 may further be arranged such that it is performed as an automated process, e.g. by automatically lowering the column into liquid nitrogen and moving it from there into a heating arrangement.

According to the preferred embodiment of FIG. 2, block B is comprised of a reactor device 32 in which carbon-isotope dioxide is converted to carbon-isotope monoxide, a carbon dioxide removal device 34, a check-valve 36, and a carbon monoxide trapping device 38, which all are connected in a line.

In the preferred embodiment the reactor device 32 is a reactor furnace comprising a material that when heated to the right temperature interval converts carbon-isotope dioxide to carbon-isotope monoxide. A broad range of different materials with the ability to convert carbon dioxide into carbon monoxide may be used, e.g. zinc or molybdenum or any other element or compound with similar reductive properties. If the reactor device 32 is a zinc furnace it should be heated to 350 to 400° C., and it is important that the temperature is regulated with high precision. The melting point of zinc is 420° C. and the zinc-furnace quickly loses it ability to transform carbon dioxide into carbon monoxide when the temperature reaches over 410° C., probably due to changed surface properties. The material should be efficient in relation to its amount to ensure that a small amount can be used, which will minimize the time needed to transfer radioactivity from the carbon dioxide trapping device 8 to the subsequent carbon monoxide trapping device 38. The amount of material in the furnace should be large enough to ensure a practical life-time for the furnace (at least several days). In the case of zinc granulates, the volume should be 100-1000 µl.

The carbon dioxide removal device 34 is used to remove traces of carbon-isotope dioxide from the gas mixture exiting the reactor device 32. In the carbon dioxide removal device 34, carbon-isotope dioxide is trapped but not carbon-isotope monoxide nor the carrier gas. The carbon dioxide removal device 34 may be comprised of a column containing ascarite® (i.e. sodium hydroxide on silica). Carbon-isotope dioxide that has not reacted in the reactor device 32 is trapped in this column (it reacts with sodium hydroxide and turns into sodium carbonate), while carbon-isotope monoxide passes through. The radioactivity in the carbon dioxide removal device 34 is monitored as a high value indicates that the reactor device 32 is not functioning properly.

Like the carbon dioxide trapping device 8, the carbon monoxide trapping device 38, has a trapping and a releasing state. In the trapping state carbon-isotope monoxide is selectively trapped but not said carrier gas, and in the releasing state said trapped carbon-isotope monoxide is released in a controlled manner. This may preferably be achieved by using a cold trap, such as a column containing silica or materials of similar properties, such as molecular sieves. Such a cold trap selectively traps carbon monoxide in a cold state below −100° C., e.g. −196° C. as in liquid nitrogen or −186° C. as in liquid argon, and releases the trapped carbon monoxide in a warm state (e.g. +50° C.). The trapping behavior of the silica-column is related to dipole-dipole interactions or possibly Van der Waal interactions. The ability of the silica-column to trap carbon-isotope monoxide is reduced if the helium, carrying the radioactivity, contains nitrogen. A rationale is that since the physical properties of nitrogen are similar to carbon monoxide, nitrogen competes with carbon monoxide for the trapping sites on the silica.

According to the preferred embodiment of FIG. 2, block C is comprised of a first and a second reaction chamber valve V3 and V4, the aforementioned reaction chamber 50, a reagent valve V5, an injection loop 70 and a solvent valve V6.

The first reaction chamber valve V3 has a gas mixture inlet 40 connected to the carbon monoxide trapping device 38, a stop position 42, a collection outlet 44, a waste outlet 46, and a reaction chamber connection port 48 connected to a gas inlet 52 of the reaction chamber 50. The first reaction chamber valve V3 has four modes of operation A to D. The reaction chamber connection port 48 is: in mode A connected to the gas mixture inlet 40, in mode B connected to the stop position 42, in mode C connected to the collection outlet 44, and in mode D connected to the waste outlet 46.

Figure 3A:
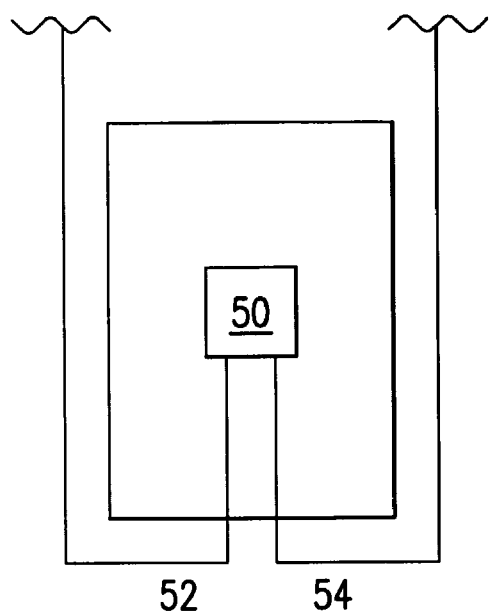
FIGS. 3a and 3b show alternative embodiments of a reaction chamber according to the invention.
Figure 3B:
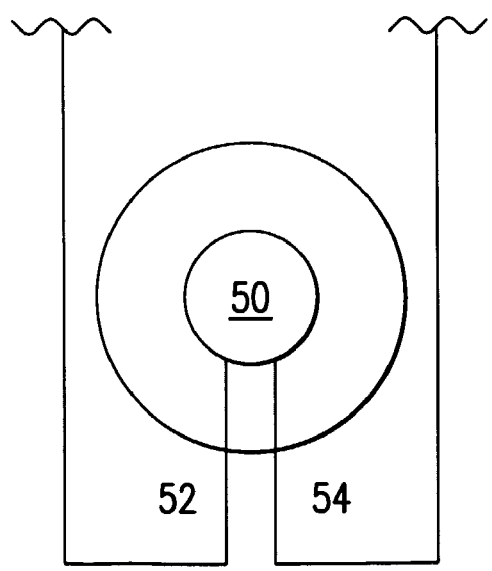

The reaction chamber 50 (micro-autoclave) has a gas inlet 52 and a liquid inlet 54, which are arranged such that they terminate at the bottom surface of the chamber. Gas inlet 52 may also be used as product outlet after the labeling is finished. During operation the carbon-isotope monoxide enriched gas mixture is introduced into the reaction chamber 50 through the gas inlet 52, where after the liquid reagent at high pressure enters the reaction chamber 50 through the liquid inlet 54. FIGS. 3a and 3b shows schematic views of two preferred reaction chambers 50 in cross section. FIG. 3a is a cylindrical chamber which is fairly easy to produce, whereas the spherical chamber of FIG. 3b is the most preferred embodiment, as the surface area to volume-ratio of the chamber is further minimized. A minimal surface area to volume-ratio optimizes the recovery of labeled product and minimizes possible reactions with the surface material. Due to the "diving-bell construction" of the reaction chamber 50, both the gas inlet 52 and the liquid inlet 54 becomes liquid-filled and the reaction chamber 50 is filled from the bottom upwards. The gas-volume containing the carbon-isotope monoxide is thus trapped and given efficient contact with the reaction mixture. Since the final pressure of the liquid is approximately 80 times higher than the original gas pressure, the final gas volume will be less than 2% of the liquid volume according to the general gas-law. Thus, a pseudo one-phase system will result. In the instant application, the term "pseudo one-phase system" means a closed volume with a small surface area to volume-ratio containing >96% liquid and <4% gas at pressures exceeding 200 bar. In most syntheses the transfer of carbon monoxide from the gas-phase to the liquid phase will probably not be the rate limiting step. After the labeling is finished the labeled volume is nearly quantitatively transferred from the reaction chamber by the internal pressure via the gas inlet/product outlet 52 and the first reaction chamber valve V3 in position C.

The second reaction chamber valve V4 has a reaction chamber connection port 56, a waste outlet 58, and a reagent inlet 60. The second reaction chamber valve V4 has two modes of operation A and B. The reaction chamber connection port 56 is: in mode A connected to the waste outlet 58, and in mode B it is connected to the reagent inlet 60.

The reagent valve V8, has a reagent outlet 96 connected to the reagent inlet 60 of the second reaction chamber valve V4, an injection loop inlet 104 and outlet 98 between which the injection loop 108 is connected, a waste outlet 100, a reagent inlet 102 connected to a reagent source, and a solvent inlet 106. The reagent valve V8, has two modes of operation A and B. In mode A, the reagent inlet 102 is connected to the injection loop inlet 104, and the injection loop outlet 98 is connected to the waste outlet 100, whereby a reagent may be fed into the injection loop 108. In mode B, the solvent inlet 106 is connected to the injection loop inlet 104, and the injection loop outlet 98 is connected to the reagent outlet 96, whereby reagent stored in the injection loop 108 may be forced via the second reaction chamber valve V4 into the reaction chamber 50, if a high pressure is applied on the solvent inlet 106.

The reagent valve V7, has a reagent outlet 82 connected to the solvent inlet 106 of the reagent valve V8, an injection loop inlet 90 and outlet 84 between which the injection loop 94 is connected, a waste outlet 86, a reagent inlet 88 connected to a reagent source, and a solvent inlet 92. The reagent valve V7, has two modes of operation A and B. In mode A, the reagent inlet 88 is connected to the injection loop inlet 90, and injection loop outlet 84 is connected to the waste outlet 86, whereby a reagent may be fed into the injection loop 94. In mode B, the solvent inlet 92 is connected to the injection loop inlet 90, and the injection loop outlet 84 is connected to the reagent outlet 82, whereby reagent stored in the injection loop 94 may be forced via the reagent valve V8 and the second reaction chamber valve V4 into the reaction chamber 50 if a high pressure is applied on the solvent inlet 92.

The reagent valve V5, has a reagent outlet 62 connected to the reagent inlet 92 of the reagent valve V8, an injection loop inlet 64 and outlet 66 between which the injection loop 70 is connected, a waste outlet 68, a reagent inlet 71 connected to a reagent source, and a solvent inlet 72. The reagent valve V5, has two modes of operation A and B. In mode A the reagent inlet 71 is connected to the injection loop inlet 64, and the injection loop outlet 66 is connected to the waste outlet 68, whereby a reagent may be fed into the injection loop 70. In mode B the solvent inlet 72 is connected to the injection loop inlet 64, and the injection loop outlet 66 is connected to the reagent outlet 62, whereby reagent stored in the injection loop 70 may be forced via the reagent valve V7, the reagent valve V8 and the second reaction chamber valve V4 into the reaction chamber 50 if a high pressure is applied on the solvent inlet 72.

The solvent valve V6, has a solvent outlet 74 connected to the solvent inlet 72 of the reagent valve V5, a stop position 76, a waste outlet 78, and a solvent inlet 80 connected to a solvent supplying HPLC-pump (High Performance Liquid Chromatography) or any liquid-pump capable of pumping organic solvents at 0-10 ml/min at pressures up to 400 bar (not shown). The solvent valve V6, has two modes of operation A and B. In mode A the solvent outlet 74 is connected to the stop position 76, and the solvent inlet 80 is connected to the waste outlet 78. In mode B the solvent outlet 74 is connected to the solvent inlet 80, whereby solvent may be pumped into the system at high pressure by the HPLC-pump.

Except for the small volume of silica in the carbon monoxide trapping devise 38, an important difference in comparison to the carbon dioxide trapping device 8, as well as to all related prior art, is the procedure used for releasing the carbon monoxide. After the trapping of carbon monoxide on carbon monoxide trapping devise 8, valve V3 is changed from position A to B to stop the flow from the carbon monoxide trapping devise 38 and increase the gas-pressure on the carbon monoxide trapping devise 38 to the set feeding gas pressure (3-5 bar). The carbon monoxide trapping devise 38 is then heated to release the carbon monoxide from the silica surface while not significantly expanding the volume of carbon monoxide in the carrier gas. Valve V4 is changed from position A to B and valve V3 is then changed from position B to A. At this instance the carbon monoxide is rapidly and almost quantitatively transferred in a well-defined micro-plug into the reaction chamber 50. Micro-plug is defined as a gas volume less than 10% of the volume of the reaction chamber 50, containing the topical substance (e.g. 1-20 µL). This unique method for efficient mass-transfer to a small reaction chamber 50, having a closed outlet, has the following prerequisites:

A micro-column 38 defined as follows should be used. The volume of the trapping material (e.g. silica) should be large enough to efficiently trap (>95%) the carbon-isotope monoxide, and small enough (<1% of the volume of a subsequent reaction chamber 50) to allow maximal concentration of the carbon-isotope monoxide. In the case of silica and a reaction chamber 50 volume of 200 µl, the silica volume should be 0.1-2 µl.

The dead volumes of the tubing and valve(s) connecting the silica column and the reaction chamber 50 should be minimal (<10% of the micro-autoclave volume).

The pressure of the carrier gas should be 3-5 times higher than the pressure in the reaction chamber 50 before transfer (1 atm.).

In one specific preferred embodiment specifications, materials and components are chosen as follows. High pressure valves from Valco®, Reodyne® or Cheminert® are used. Stainless steel tubing with o.d. 1/16" is used except for the connections to the porapac-column 8, the silica-column 38 and the reaction chamber 50 where stainless steel tubing with o.d. 1/32" are used in order to facilitate the translation movement. The connections between V1, V2 and V3 should have an inner diameter of 0.2-1 mm. The requirement is that the inner diameter should be large enough not to obstruct the possibility to achieve the optimal flow of He (2-50 ml/min) through the system, and small enough not to prolong the time needed to transfer the radioactivity from the porapac-column 8 to the silica-column 38. The dead volume of the connection between V3 and the autoclave should be minimized (<10% of the autoclave volume). The inner diameter (0.05-0.1 mm) of the connection must be large enough to allow optimal He flow (2-50 ml/min). The dead volume of the connection between V4 and V5 should be less than 10% of the autoclave volume.

When column 8 is a porapac-column, it is preferably comprised of a stainless steel tube (o.d.=1/8", i.d.=2 mm, l=20 mm) filled with Porapac Q® and fitted with stainless steel screens. The silica-column 38 preferably is comprised of a stainless steel tube (o.d=1/16", i.d.=0.1 mm) with a cavity (d=1 mm, h=1 mm, V=0.8 µl) in the end. The cavity is filled with silica powder (100/80 mesh) of GC-stationary phase type. The end of the column is fitted against a stainless steel screen.

It should be noted that a broad range of different materials could be used in the trapping devices. If a GC-material is chosen, the criterions should be good retardation and good peak-shape for carbon dioxide and carbon monoxide respectively. The latter will ensure optimal recovery of the radioactivity.

Below a detailed description is given of a method of producing carbon-isotope using an exemplary system as described above.

Preparations of the system are performed by the steps 1 to 7:

1. V1 in position A, V2 in position A, V3 in position A, V4 in position A, helium flow on with a max pressure of 5 bar. With this setting, the helium flow goes through the [$^{11}$C]carbon dioxide trapping column, the zinc furnace, the [$^{11}$C] carbon monoxide trapping column, the reaction chamber 50 and out through V4. The system is conditioned, the reaction chamber 50 is rid of solvent and it can be checked that helium can be flowed through the system with at least 10 ml/min.
2. The zinc-furnace is turned on and set at 400° C.
3. The [$^{11}$C]carbon dioxide and [$^{11}$C]carbon monoxide trapping columns are cooled with liquid nitrogen. At −196° C., the porapac-and silica-column efficiently traps carbon-isotope dioxide and carbon-isotope monoxide respectively.
4. V5 in position A (load). The injection loop (250 µl), attached to V5, is loaded with the reaction mixture, or when the substrate is in gas form, a solution of transition metal complex.
5. V7 in position A (load). The injection loop (250-1000 µl), attached to V7, is loaded with $H_2$ gas, when used.
6. V8 in position A (load). The injection loop (250-1000 µl), attached to V8, is loaded with a substrate when it is in gas form.
7. The HPLC-pump is attached to a flask with freshly distilled THF (or other high quality solvent) and primed. V6 in position A.

Production of carbon-isotope dioxide may be performed by the steps 8 to 9:

8. Carbon-isotope dioxide is produced using the 14N(p,α) $^{11}$C reaction in a target gas containing nitrogen (AGA, Nitrogen 6.0) and 0.1% oxygen (AGA. Oxygen 4.8), bombarded with 17 MeV protons.
9. The carbon-isotope dioxide is transferred to the apparatus using nitrogen with a flow of 100 ml/min.

Synthesis of carbon-isotope may thereafter be performed by the steps 10 to 19:

10. V1 in position B and V2 in position B. The nitrogen flow containing the carbon-isotope dioxide is now directed through the porapac-column (cooled to −196° C.) and out through a waste line. The radioactivity trapped in the porapac-column is monitored.
11. When the radioactivity has peaked, V1 is changed to position A. Now a helium flow is directed through the porapac-column and out through the waste line. By this operation the tubings and the porapac-column are rid of nitrogen.
12. V2 in position A and the porapac-column is warmed to about 50° C. The radioactivity is now released from the porapac-column and transferred with a helium flow of 10 ml/min into the zinc-furnace where it is transformed into carbon-isotope monoxide.
13. Before reaching the silica-column (cooled to −196° C.), the gas flow passes the ascarite-column. The carbon-isotope monoxide is now trapped on the silica-column. The radioactivity in the silica-column is monitored and when the value has peaked, V3 is set to position B and then V4 is set to position B.
14. The silica-column is heated to approximately 50° C., which releases the carbon-isotope monoxide. V3 is set to position A and the carbon-isotope monoxide is transferred to the reaction chamber 50 within 15 s.
15. V3 is set to position B, V5 is set to position B, V7 is set to position B, V8 is set to position 8, the HPLC-pump is turned on (flow 7 ml/min) and V6 is set to position B. Using the pressurized THF (or other solvent), the reaction mixture is transferred to the reaction chamber 50. When the HPLC-pump has reached its set pressure limit (e.g 40 Mpa), it is automatically turned off and then V6 is set to position A.
16. The reaction chamber 50 is moved into the cavity of a heating block containing a high boiling liquid (e.g. polyethylene glycol or mineral oil). The temperature of the heating block is usually in the range of 100-200° C.
17. After a sufficient reaction-time (usually 5 min), V3 is set to position C and the content of the reaction chamber 50 is transferred to a collection vial.
18. The reaction chamber 50 can be rinsed by the following procedure: V3 is set to position B, the HPLC-pump is turned on, V6 is set to position B and when maximal pressure is reached V6 is set to position A and V3 is set to position 3 thereby transferring the rinse volume to the collection vial.
19. The labeled product obtained in step 18 may then be subsequently reduced and then substituted in the collection vial to obtain desired labeled organohalides.

The synthesis of labeled organohalides, such as [1-$^{11}$-C] ethyl iodide, [1-$^{11}$-C]propyl iodide and [$^{11}$C]aryl halides, prepared from [$^{11}$C]carbon dioxide and a Grignard reagent has been described in the literature. Isotopic dilution originating from carbon dioxide in the environment is a potential drawback of the Grignard method. Careful preparation and handling of the Grignard reagent is required in order to maximize the specific radioactivity of the labeled organohalides. The instant invention utilizes [$^{11}$C]carbon monoxide and presents an efficient method to synthesize labeled organohalides. The invention overcomes the limitations of the Grignard method in respect to specific radioactivity. The low atmospheric concentration of carbon monoxide compared to carbon dioxide makes it more advantageous to use [$^{11}$C]carbon monoxide than [$^{11}$C]carbon dioxide when synthesizing labeled products which are aimed to have high specific radioactivity. The syntheses of labeled organohalides from [$^{11}$C] carbon monoxide consist of three reaction steps:

Carbonylation

Reduction

Substitution/Halogenation

The precursors used in the carbonylation reaction together with [$^{11}$C]carbon monoxide are olefins, acetylenes, alkyl halides and triflates, and aromatic halides and triflates. Other reagents, used as nucleophile sources, are selected from a list comprising of: $H_2O$, ROH and $H_2$ where R is independently linear or cyclic lower alkyl. $H_2$ may be used alone or together with $H_2O$ or ROH, since it has shown to increase yield and purity of the labeled organohalide when used as an additive. A base, e.g. tetrabutylammonium hydroxide, may also be added to activate the nucleophiles when alkyl halides and triflates, or aromatic halides and triflates, are used as precursors in the carbonylation reaction.

The labeled products obtained in the carbonylation reaction are reduced to alkoxides and subsequently converted to organohalides.

When alkyl- or aromatic halide or triflate are used as substrates, the substrates have the formula of R'$_1$—X', and the resultant labeled organohalides have the formula of

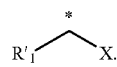

The general reaction scheme for the synthesis is illustrated below:

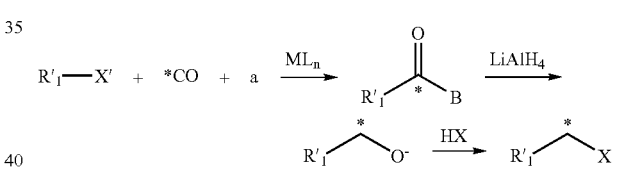

wherein a is $H_2$ gas or HOR with optional base, B is H or OR, R'$_1$ is defined as independently linear or cyclic lower alkyl or substituted aryl with Cl, F or —OR, X' is I, Br or OTf, X is I or Br, M is Pd, Rh, Co, Pt or Ru, L is phosphine ligand and R is defined as independently linear or lower cyclic alkyl or aryl.

When olefin is sued as a substrate, the substrate has the formula of

and the resultant labeled organohalides have the formula of

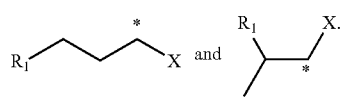

The general reaction scheme for the synthesis is illustrated below:

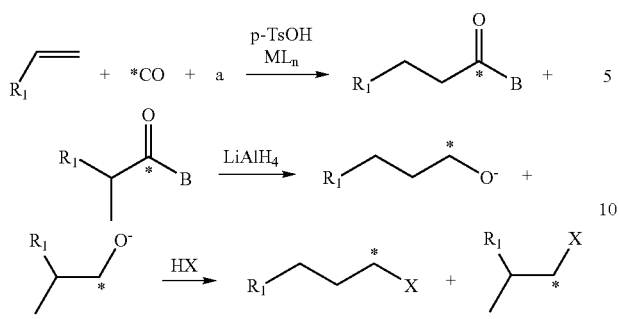

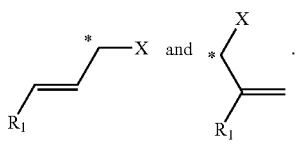

wherein a is $H_2$ gas or HOR with optional base, B is H or OR, $R_1$ is defined as independently linear or cyclic lower alkyl or aryl, X is I or Br, M is Pd, Rh, Co, Pt or Ru, L is phosphine ligand, p-TsOH is p-toluenesulfonic acid, and R is defined as independently linear or lower cyclic alkyl or aryl.

When acetylene is used as substrates, there are two reaction schemes. Under the first reaction scheme, the substrate has the formula

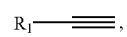

and the resultant organohalides have the formula of

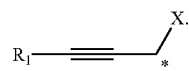

The reaction scheme is illustrated below:

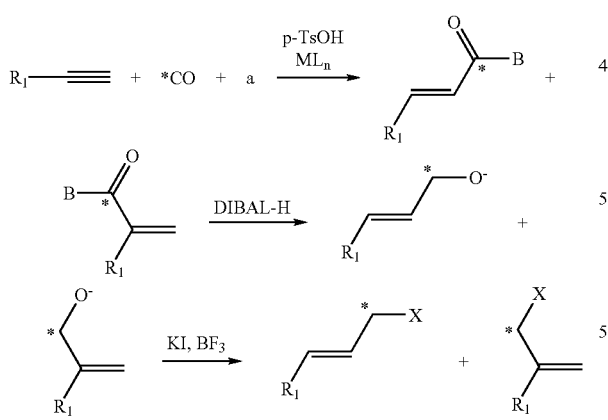

wherein a is $H_2$ gas or HOR and/or $H_2O$ with optional base, B is H and/or OH, or OR and/or OH, $R_1$ is defined as independently linear or cyclic lower alkyl or aryl, X is I or Br, M is Pd, Rh, Co, Pt or Ru, L is phosphine ligand, p-TsOH is p-toluenesulfonic acid, DIBAL-H is diisobutylaluminiumhydride, and R is defined as independently linear or lower cyclic alkyl or aryl.

Under the second reaction scheme, the substrate has the formula $$R_1 \!\!-\!\!\!\equiv,$$

and the resultant organohalides have the formula of

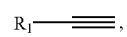

The reaction scheme is illustrated as below:

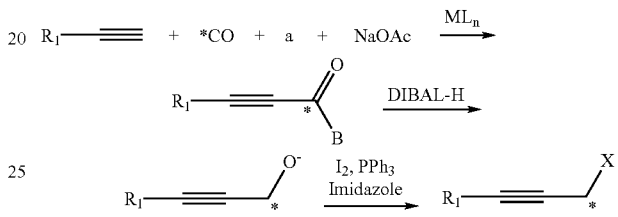

wherein a is $H_2$ gas or HOR and/or $H_2O$ with optional base, B is H and/or OH, or OR and/or OH, $R_1$ is defined as independently linear or cyclic lower alkyl or aryl, X is I or Br, M is Pd, Rh, Co, Pt or Ru, L is phosphine ligand, NaOAc is sodium acetate, DIBAL-H is diisobutylaluminiumhydride, and R is defined as independently linear or lower cyclic alkyl or aryl.

Several applications for synthesizing useful PET tracers may then be accomplished through the use of the labeled organohalides as alkylating agents. Some examples are illustrated below.

O-nucleophilic Reactions

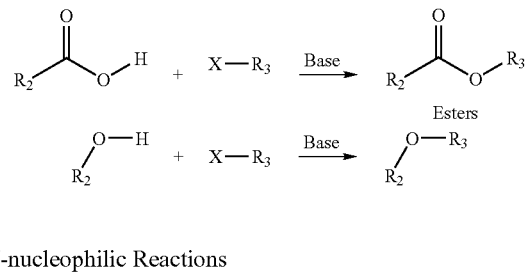

N-nucleophilic Reactions

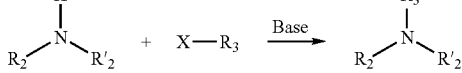

S-nucleophilic Reactions

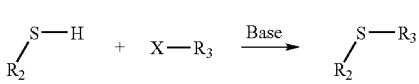

wherein $X-R_3$ is a $^{11}C$-Labeled organohalide, $R_2$ is defined as independently substituted linear or cyclic alkyl or aryl, $R'_2$ is defined as hydrogen or independently substituted linear or cyclic alkyl or aryl, and X is a halogen.

Metal Mediated Reactions

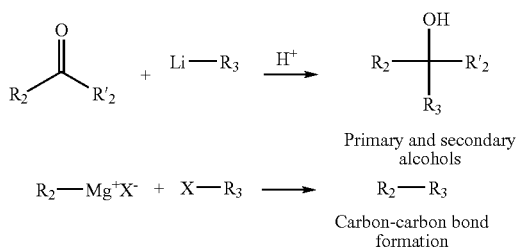

Primary and secondary alcohols

Carbon-carbon bond formation wherein $X-R_3$ is a $^{11}C$-Labeled organohalide, $Li-R_3$ is a $^{121}C$-Labeled organolithium compound, $R_2$ and $R'_2$ are defined as independently substituted linear or cyclic alkyl or aryl, and X is a halogen.

They provide valuable PET tracers in various PET studies. In an embodiment of the present invention, it provides kits for use as PET tracers comprising [$^{11}C$]-labeled compounds.

Such kits are designed to give sterile products suitable for human administration, e.g. direct injection into the bloodstream. Suitable kits comprise containers (e.g. septum-sealed vials) containing the adrenergic interfering agent and precursor of the adrenergic imaging agent.

The kits may optionally further comprise additional components such as radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the pharmaceutical composition post-reconstitution, i.e. in the radioactive diagnostic product itself. The antimicrobial preservative may, however, also optionally be used to inhibit the growth of potentially harmful micro-organisms in one or more components of the kit of the present invention prior to reconstitution. Suitable antimicrobial preservatives include: the parabens, i.e., ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the ligand conjugate is employed in acid salt form, the pH-adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

EXAMPLES

The invention is further described in the following examples which are in no way intended to limit the scope of the invention.

Example 1

Experimental Setup

[$^{11}C$]Carbon dioxide production was performed using a Scanditronix MC-17 cyclotron at Uppsala IMANET. The $^{14}N(p,\alpha)^{11}C$ reaction was employed in a gas target containing nitrogen (Nitrogen 6.0) and 0.1% oxygen (Oxygen 4.8) which was bombarded with 17 MeV protons.

[$^{11}C$]Carbon monoxide was obtained by reduction of [$^{11}C$] carbon dioxide as described in the instant application.

The syntheses with [$^{11}C$]carbon monoxide were performed with an automated module as part of the system "Synthia 2000". [$^{11}C$]carbon dioxide was trapped on a column (Porapac Q) at $-196°$ C. and released by heating and reduced during its passage through a zinc filled tube at $400°$ C. HPLC analysis was performed with a Beckman 126-gradient pump and a Beckman 166 variable wavelength UV-detector in series with a $\beta^+$-flow detector. The analytical column was a Beckman Ultrasphere ODS $C_{18}$ (250×4.6 mm id).

Example 2

Synthesis of [1-$^{11}C$] Ethyl Iodide

The general reaction scheme is illustrated as follows:

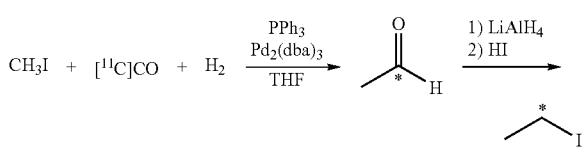

Alternatively, when acids are obtained due to small amount of water in the reagents, the reaction scheme becomes:

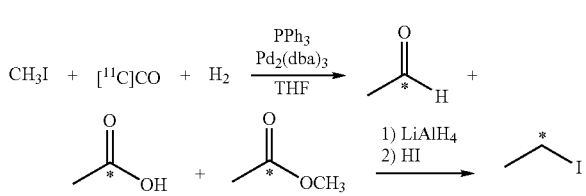

Tris(dibenzylideneacetone)dipalladium(0) (0.80 mg, 0.87 µmol) and triphenylphosphine (2.7 mg, 10.3 µmol, 12 equiv.) were placed in a 0.8 ml vial equipped with a rubber septum. THF (360 µl) was added and the resulting solution was degassed with argon. Methyl iodide (1.0 μl, 16 μmol, 18 equiv.) was added. The solution was loaded into an injection valve loop. A second injection valve loop was loaded with hydrogen gas (1.0 ml, 1 atm.). THF was pumped through the two injection loops and the reagents were pumped into a 200 μl Teflon coated stainless steel micro-autoclave containing [$^{11}$C]CO. The micro-autoclave was heated for 5 min at 120° C. The reaction mixture was transferred to a 2 ml septum-equipped evacuated glass vial containing lithium aluminium hydride (100 μl, 1 M). The vial was heated at 120° C. for 2-3 min during the removal of THF under a stream of nitrogen gas. Then the vial was cooled down to sub-zero temperature. Hydriodic acid (1.0 ml, 57 wt. % in water) was added and the vial was heated for 5 min at 120° C. The vial was removed from the heating and [1-$^{11}$C]ethyl iodide was transferred in a stream of nitrogen gas (20 ml/min) through a drying tower (phosphorus pentoxide desiccant) to a trapping vessel. Analytical LC was used to assess the identity and radiochemical purity. Radiochemical yield of [1-$^{11}$C]ethyl iodide was 66±6% with a radiochemical purity of 87±2%. [$^{11}$C]Methyl iodide was the only radiochemical by-product.

Example 3

Synthesis of (R)-[O-ethyl-1-$^{11}$C]Etomidate

In a 0.8 ml glass vial equipped with a rubber septum, (R)-3-(1-phenyl-ethyl)-3H-imidazole-4-carboxylic acid (1.2 mg, 5.5 μmol) was dissolved in dichloromethane (200 μl) at room temperature. Tetrabutylammonium hydroxide in methanol (4.8 μl, 1 M, 4.8 μmol) was added. The vial was gently heated and the solvent was thoroughly removed under a stream of nitrogen gas. Dimethylformamide (300 μl) was added. [1-$^{11}$C]Ethyl iodide, prepared as described above, was transferred in a flow of nitrogen gas (20 ml/min) to the glass vial and bubbled through the solution. The vial was heated for 5 min at 120° C. The reaction mixture was injected onto a semi-preparative HPLC column and (R)-[O-ethyl-1-$^{11}$C]Etomidate was isolated. Mobile phase A1:B2 (52:48). Flow 4 ml min$^{31\ 1}$. R.t 12.1.-13.5 min. Analytical LC was used to assess the identity and radiochemical purity. Mobile phase A1:B2 (45:55). Flow 1.5 ml min$^{-1}$. R.t. 8.4 min. Radiochemical purity >99%.

Example 3

Synthesis of [1-$^{11}$C] Propyl Iodide

The general reaction scheme is illustrated as follows:

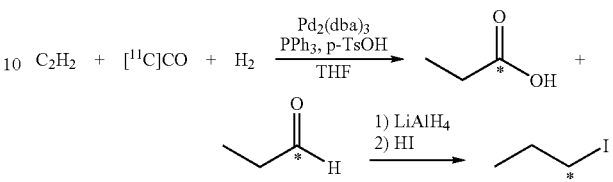

Or alternatively:

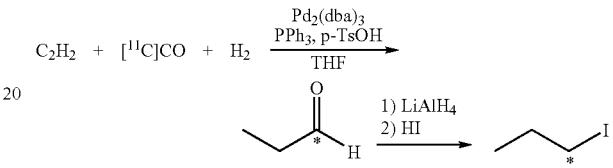

Tris(dibenzylideneacetone)dipalladium(0) (0.7 mg, 0.76 μmol), triphenylphosphine (2.7 mg, 10.3 μmol, 12 equiv.) and p-toluenesulfonic acid (3.9 mg, 20.5 μmol) were placed in a 0.8 ml vial equipped with rubber septum. THF (360 μl) was added and the resulting solution was degassed with argon. The solution was loaded into an injection valve loop. A second injection valve loop was loaded with ethene (1.0 ml, 1 atm.). A third injection valve loop was loaded with hydrogen gas (0.7 ml, 1 atm.). THF was pumped through all three injection loops and the reagents were pumped into a 200 μl Teflon coated stainless steel micro-autoclave containing [$^{11}$C]CO. The reagents were contained in the autoclave for 5 min at room temperature. Then the reaction mixture was transferred to a 2 ml septa-equipped evacuated glass vial containing lithium aluminium hydride (100 μl, 1 M). The vial was heated at 120° C. for 2-3 min during the removal of THF under a stream of nitrogen gas. Then the vial was cooled down to sub-zero temperature. Hydriodic acid (1.0 ml, 57 wt. % in water) was added and the vial was heated for 5 min at 120° C. The vial was removed from the heat source and [1-$^{11}$C]propyl iodide was transferred in a stream of nitrogen (20 ml/minute) through a drying tower (phosphorus pentoxide desiccant) to a

| Substrate | Product | Initial Radioactivity $^{11}$CO (GBq) | Yield$^a$ (%) | Product Amount (nmol) | Specific Radioactivity (GBq/μmol) |
|---|---|---|---|---|---|
| 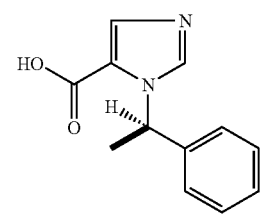 | 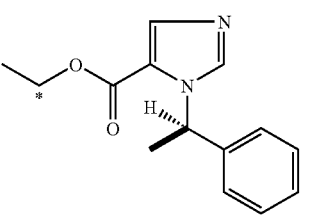 | 2.5 ± 0.5<br>7<br>10 | 45 ± 0.5<br>25<br>22 | 31 ± 6<br>15<br>15 | 8.4 ± 1.2<br>22<br>36 |

$^a$Isolated decay-corrected radiochemical yield calculated from the initial amount of radioactivity used in the [1-$^{11}$C]ethyl iodide synthesis trapping vessel. Analytical LC was used to assess the identity and radiochemical purity. Radiochemical yield of [1-$^{11}$C] propyl iodide was 58±4% based on [$^{11}$C]carbon monoxide. The radiochemical purity was 93±2%. [$^{11}$C]Methyl iodide was the only radiochemical by-product.

Specific Embodiments, Citation of References

The present invention is not to be limited in scope by specific embodiments described herein. Indeed, various modifications of the inventions in addition to those described herein will become apparent to these skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method for labeling synthesis of organohalides, comprising:
   (a) providing a high pressure reaction chamber having a liquid/gas inlet and a gas inlet in a bottom surface thereof,
   (b) providing a substrate solution to be labeled mixed with a transition metal complex,
   (c) providing H$_2$ gas or HOR, with optional water, where R is independently linear or lower cyclic alkyl or aryl,
   (d) introducing a carbon-isotope monoxide enriched gas-mixture into the reaction chamber via the gas inlet,
   (e) introducing at high-pressure said H$_2$ gas or HOR, with optional water, into the reaction chamber via the liquid/gas inlet,
   (f) introducing at high-pressure said substrate solution mixed with transition metal complex into the reaction chamber via the liquid/gas inlet,
   (g) waiting a predetermined time while the labeling synthesis occur, and
   (h) removing the labeled compounds from the reaction chamber,
   (i) reducing the labeled compounds to alcohol,
   (j) substituting with a halogen atom to obtain the labeled organohalides.

2. A method of claim 1, wherein the carbon-isotope monoxide enriched gas-mixture is produced by a method comprising:
   (a) providing carbon-isotope dioxide in a suitable carrier gas,
   (b) converting carbon-isotope dioxide to carbon-isotope monoxide by introducing said gas mixture in a reactor device,
   (c) trapping carbon-isotope monoxide in a carbon monoxide trapping device, wherein carbon-isotope monoxide is trapped but not said carrier gas, and
   (d) releasing said trapped carbon-isotope monoxide from said trapping device in a well defined micro-plug, whereby a volume of carbon-isotope monoxide enriched gas-mixture is achieved.

3. A method of claim 1, wherein the carbon-isotope is $^{11}$C, $^{13}$C, or $^{14}$C.

4. A method of claim 1, wherein the carbon-isotope is $^{11}$C.

5. A method of claim 1, wherein the step of introducing the substrate solution mixed with a transitional metal complex is performed using a pressure that is about 80 times higher than the pressure before the introduction, in order to maintain a pseudo one-phase system.

6. A method of claim 1, wherein the step of waiting a predetermined time comprises adjusting the temperature of the reaction chamber to enhance the labeling synthesis.

7. A method of claim 1, wherein the transitional metal complex is selected from a group of transition metal complex comprising Pd, Rh, Co, Pt or Ru.

8. A method of claim 1, wherein the substrate is alkyl- or aromatic halide or triflate, olefin or acetylene.

9. A method of claim 8, wherein the substrate is alkyl- or aromatic halide or triflate having the formula of R'$_1$—X', wherein R'$_1$ is defined as independently linear or cyclic lower alkyl or substituted aryl with Cl, F or —OR, and X' is I, Br or OTf.

10. Labeled organohalides generated according to a method of claim 9 having the formula of

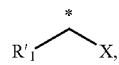

wherein R'$_1$ is defined as independently linear or cyclic lower alkyl or substituted aryl with Cl, F or —OR, X' is I, Br or OTf, X is I or Br.

11. A method of claim 8, wherein the substrate is olefin having the formula of

wherein R$_1$ is defined as independently linear or cyclic lower alkyl or aryl.

12. A method of claim 8, wherein the substrate is acetylene having the formula of

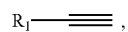

wherein R$_1$ is defined as independently linear or cyclic lower alkyl or aryl.

13. A method of claim 12, wherein only water is used in step (c).

* * * * *